United States Patent [19]

Day et al.

[11] Patent Number: 4,889,707

[45] Date of Patent: Dec. 26, 1989

[54] COMPOSITION AND METHOD FOR RADIATION SYNOVECTOMY OF ARTHRITIC JOINTS

[75] Inventors: Delbert E. Day, Rolla; Gary J. Ehrhardt, Columbia, both of Mo.

[73] Assignee: The Curators of the University of Missouri, Columbia, Mo.

[21] Appl. No.: 150,154

[22] Filed: Jan. 29, 1988

[51] Int. Cl.$^4$ .......................... A61K 43/00; A61B 6/00
[52] U.S. Cl. ....................................... 424/1.1; 252/625; 252/644; 128/654; 600/3
[58] Field of Search .................. 424/1.1; 252/625, 644; 534/10; 600/3; 128/654

[56] References Cited

U.S. PATENT DOCUMENTS

| | | | |
|---|---|---|---|
| 3,474,777 | 10/1969 | Figge et al. | 128/2 |
| 4,135,935 | 1/1979 | Pfeil et al. | 106/35 |
| 4,333,847 | 6/1982 | Tran et al. | 252/269 |
| 4,349,025 | 9/1982 | Drake | 128/260 |
| 4,350,675 | 9/1982 | Drake | 424/1 |
| 4,362,659 | 12/1982 | Macedo et al. | 252/629 |
| 4,517,006 | 5/1985 | Drake et al. | 71/64.11 |
| 4,530,840 | 7/1985 | Tice et al. | 514/179 |
| 4,745,907 | 5/1988 | Russel, Jr. et al. | 128/1.1 |
| 4,752,464 | 6/1988 | Lieberman et al. | 424/1.1 |
| 4,789,501 | 12/1988 | Day et al. | 252/645 |

FOREIGN PATENT DOCUMENTS 8603124  6/1986  World Int. Prop. O. ........... 424/1.1

OTHER PUBLICATIONS

Intra-articular Radiation Synovectomy, Sledge et al., Clinical Orthopaedics and Related Research, 37-40, No. 182, Jan.-Feb., 1984.

Radcliffe, J. H. et al., "Albumin Microspheres for Intra-Articular Drug Delivery", J. Pharm. Pharmacol., 39(4), 290-5 [C.A. 106(22): 182574].

Primary Examiner—John S. Maples
Attorney, Agent, or Firm—Senniger, Powers, Leavitt and Roedel

[57] ABSTRACT

Radioactive microspheres for radiation synovectomy of arithmetic joints in a mammal comprise a biodegradable glass material and a beta radiation emitting radioisotope chemically dissolved in and distributed substantially uniformly throughout the glass material. The biodegradable glass material may be lithium silicate, lithium aluminosilicate, lithium aluminoborate, lithium germanate, lithium aluminogermanate, potassium silicate, potassium aluminosilicate, potassium, aluminoborate, potassium germanate or potassium aluminogermanate and the beta radiation emitting radioisotope may be samarium-153, holmium-166, erbium-169, dysprosium-165, rhenium-186, rhenium-188 or yttrium-90. Methods for preparing such microspheres and for carrying out radiation synovectomy of arthritic joints utilizing such microspheres are also disclosed.

25 Claims, 2 Drawing Sheets

COMPOSITION AND METHOD FOR RADIATION SYNOVECTOMY OF ARTHRITIC JOINTS

BACKGROUND OF THE INVENTION

This invention relates to radiation synovectomy for arthritic joints and, more particularly, to novel biodegradable and biologically compatible glass microspheres or beads and their use in carrying out radiation synovectomy of arthritic joints.

Current medical management of rheumatoid arthritis includes patient education, appropriate rest and physical therapy, and the use of anti-inflammatory drugs for relief of pain and inflammation. Ruddy, S., The Management of Rheumatoid Arthritis. Textbook of Rheumatology, 2nd ed., W. B. Saunders Co. Philadelphia, 1985, p. 979. Patients who do not respond to these modalities may require therapy with anti-malarial agents such as hydroxychloroquine (Bell, C. L., Hydroxychloroquine Sulfate in Rheumatoid Arthritis: Long-Term Response Rate and Predictive Parameters, American Journal of Medicine, 75:46, 1983) or remission inducing agents including gold salts (Empire Rheumatism Council, Gold Therapy in Rheumatoid Arthritis: Final Report of a Multicentre Controlled Trial, Ann. Rheum. Dis. 20:315, 1961), penicillamine (Multicentre Trial Group: Controlled Trial of d(-) Penicillamine in Severe Rheumatoid Arthritis, Lancet, 1:275, 1973), or azathioprine (Abel, T. et al., Long-Term Effects of Azathioprine in Rheumatoid Arthritis, Arthritis Rheum. 21:539, 1978). Despite the efficacy of these drugs, patient response is variable and improvement may not occur until treatment has extended for three to six months. When a few joints remain swollen and painful and interfere with the patient's progress, intra-articular instillation of corticosteroids may be used as an adjunct to systemic therapy. This local remedy, however, may be ineffective or may last only a few days (Owen, D. S., Aspiration and Injection of Joints and Soft Tissues, Textbook of Rheumatology, supra, p. 546).

Surgery may be used in several different ways to help the patient with rheumatoid arthritis. Surgery can help relieve pain, it can prevent further deformity and loss of function, or at least allay these problems, and when destruction has occurred, reconstructive procedures can return function to a part or a limb. Sledge, C. B., Introduction to the Surgical Management of Arthritis, Textbook of Rheumatology, supra, p. 1787.

Most of the operations done on rheumatoid patients relieve pain. Fusions of joints, total joint replacement and synovectomy are examples of procedures that significantly reduce pain. Conaty (Conaty, J. P., Surgery of the Hip and Knee in Patients with Rheumatoid Arthritis, Journal of Bone and Joint Surgery, 55(A):301, 1973) states that in rheumatoid arthritis, synovectomy was the most successful procedure for preserving motion of a joint, except for total joint arthroplasty. This procedure, then, is preventive. Even so, eventually the synovium regenerates and the process continues (Patzakis, M. J. et al., A Visual, Histological, and Enzymatic Study of Regenerating Rheumatoid Synovium in the Synovectomized Knee, Journal of Bone and Joint Surgery, 55(A):287, 1973). Total joint surgery will relieve any or all of the aforementioned disabilities, but brings with it other problems that must be taken into consideration by the surgeon. Some of these are: (1) cost, (2) the risk of infection, (3) the fact that the implants may come loose and be painful, and (4) the fact that the implant may break with unusual use.

Chemical and radioisotope synovectomy (synoviorthesis) constitutes an effective alternative to operative therapy. The advantages of synoviorthesis are: (1) simple techniques employed in their use, (2) decreased or no hospitalization, (3) lower costs, (4) early and easier mobilization of the patient, and (5) a surgical synovectomy remains an alternative treatment should the synoviorthesis not work.

In general, the results of radioisotope synoviorthesis appear to be superior to those attained with chemical synovectomy. (Menkes, C. J., et al. La Synoviorthese a L'acide Osmique Chez L'hemophilie, Rev. Rhum. 40:255, 1973; Oka, M., et al., The Fate and Distribution of Intra-Articularly Injected Osmium Tetraoxide, Acta Rheum. Scand., 16:271, 1970; Delbarre, F., et al., La Synoviorthese par les Radio-Isotopes a la Main et au Poignet, Rev. Rhum., 40:205, 1973). Some chemical agents that have been used are thio-tepa (Flatt, A. E., Intra-Articular Thio-Tepa in Rheumatoid Disease of the Hands, Rheumatism, 18:70, 1962; Fearnley, M. D., Intra-Articular Thio-Tepa Therapy in Rheumatoid Arthritis, Ann. Phys. Med., 7:294, 1963; Zuckner, J., et al., Evaluation of Intra-Articular Thio-Tepa in Rheumatoid Arthritis, Ann. Rheum. Dis., 25:178, 1966; Gross, D., Chemische Synovektomie mit Senfgas bei Primar Chronischer Polyarthritis, Z. Rheumforsch, 22:456, 1963; Mondragon Kalb, M., Thiotepa en al Tratamiento de la Arthritis Rhumatoide, Medicina, 15:82, 1965), osmic acid (Menkes, C. J., et al., La Synoviorthese a L'acide Osmique Chez L'hemophilie, Rev. Rhum., 40:255, 1973; Oka, M., et al., The Fate and Distribution of Intra-Articularly Injected Osmium Tetraoxide, Acta Rheum. Scand., 16:271, 1970; Von Reis, G., et al., Intra-Articular Injections of Osmic Acid in Painful Joint Affections, Acta Med. Scand. Suppl., 259: 27, 1951; Berglof, F. E., Further Studies on the Use of Osmic Acid in the Treatment of Arthritis, Acta Rheum. Scand., 10:92, 1964; Martio, J., et al., Intra-Articular Osmic Acid in Juvenile Rheumatoid Arthritis, Scand. J. Rheumatol, 1:5, 1972; Brattstrom, H., et al., Kombinierte Chemische und Operative Synovektomie es Kniegelenks, Orthapade, 2:73, 1973; Jakubowski, S., et al., Indikatronen zur Synovektomie bei pcP, orthopade, 2:6, 1973), varicoid (Tillman, K., Chemische Synovektomie, Orthopade, 2:10, 1973) and gold (Delbarre, F., et al., supra). Radioactive substances include Gold-198, Yttrium-90 citrate, Yttrium-90 resin, Rhenium-186, Erbium-169, Yttrium-90 ferric hydroxide, Radium-224 and Phosphorus-32 chromic phosphate (Sledge, C. B., supra).

Beta-emitting radionuclides are considered the most useful for radiotherapeutic applications because of the moderate linear energy transfer (LET) of the ionizing particle (electron) and its intermediate range (typically several millimeters in tissue). In contrast, gamma rays deliver dosage at lower levels over much greater distances, thus hampering the localization of the dose and diluting its effect. Alpha particles represent the other extreme; they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated.

It is fortuitous that beta emitters, the most useful radiotherapeutic radionuclides, are also the ones most copiously produced by neutron capture in nuclear reactors, the most powerful sources of radioisotopes. Reactor-produced isotopes number in the thousands, giving researchers a wide choice of isotopes of various half-lives, beta energies, gamma emissions, and chemical properties. Gamma emissions, while not as useful for therapy as beta emissions, play an important role in that they permit the distribution of radioisotope in the body to be observed using an Anger gamma ray camera or single photon computed tomography (SPECT) instrument. This permits direct observation and, to some extent, quantification of radionuclide leakage from an organ or a joint and also provides positive verification of the potency of joint injection and distribution of the radionuclide in the research animal.

Treatment of the different depths of diseased synovium in joints of disparate size, such as the finger joints and the knee, requires isotopes of different average beta range. It is important to achieve a "kill" of sufficient depth to be efficacious without causing significant necrosis of overlying normal tissues.

The effectiveness of a radioisotope depends upon the fact that it gives off beta radiation which kills tissue along with the fact that it gives off no alpha and little gamma radiation. The latter type of radiation penetrates too far, affecting tissues adversely, whereas beta radiation has a short penetration distance, varying in millimeters for each radioisotope. Radioisotopes also have different half-lives, some being far too long or too short for any practical use. These factors, then, have to be considered in the application of a radioisotope for synoviorthesis.

Sledge et al. (Treatment of Rheumatoid Synovitis of the Knee with Intra-Articular Injection of Dysprosium-165 Ferric Hydroxide Macroaggregates, Arthritis and Rheumatism, 29(2):153, 1986) have used macroaggregates of ferric hydroxide (FHMA) combined with dysprosium-165. This compound does present the problem of some leakage to local lymph nodes and other tissues. Also, dyprosium-165 has a half-life of 2.3 hours, making it necessary for the patient to be close to a nuclear reactor, severely limiting the use of this radioisotope. Even with these drawbacks, the clinical results were noteworthy, as 80% of patients treated for chronic synovitis of the knee with dysprosium-165-FHMA were improved at one year, and nearly 90% of patients with Stage 1 roentgenographic changes had excellent, good, or fair results (Sledge, et al., Intra-Articular Radiation Synovectomy, Clinical Orthopaedics and Related Research, 182:37, 1984). These results and the results of others (Boerbooms, A. M., et al., Radio-Synovectomy in Chronic Synovitis of the Knee Joint in Patients with Rheumatoid Arthritis, European Journal of Nuclear Medicine, 10:446, 1985; Multicentre Trial Group: Intra-Articular Radioactive Yttrium and Triamcinolone Hexacetonide: An Inconclusive Trial, Ann. Rheum. Dis., 43:620, 1984; Kyle, V., et al., Yttrium-90 Therapy and $^{99m}$Tc Pertechnetate Knee Uptake Measurements in the Management of Rheumatoid Arthritis, Annals of the Rheumatic Diseases, 42:132, 1983; Rosenthall, L., Use of Radiocolloids for Intra-Articular Therapy for Synovitis, In Therapy in Nuclear Medicine, Grune and Stratton, Inc., New York, 1978, p. 147; Spooren, P. et al., Synovectomy of the Knee with 90-Y, European Journal of Nuclear Medicine, 10:441, 1985) show that radiation synoviorthesis has a role in the treatment of inflammatory synovitis.

In our copending, coassigned application for U.S. patent Ser. No. 673,123, filed Nov. 19, 1984, now U.S. Pat. No. 4,789,501, dated Dec. 6, 1988, we disclose novel microspheres for use in the radiation therapy of liver cancer and other cancerous or tumor bearing tissue. Such microspheres have not, however, been used or suggested for use in radiation synovectomy of arthritic joints and may not be suitable for use in radiation synovectomy by reason of the radionuclides incorporated therein having relatively long physical half-lives.

There is a continuing need, therefore, for improved microspheres and methods for radiation synovectomy of arthritic joints.

SUMMARY OF THE INVENTION

Among the several objects of the invention may be noted the provision of novel microspheres for use in radiation synovectomy of arthritic joints; the provision of such microspheres containing beta emitting radioisotopes which have a moderately abundant low energy gamma photon that is in the energy range used for nuclear medicine imaging; the provision of such microspheres which are biodegradable and advantageously gradually dissolve after they are no longer radioactive; the provision of such microspheres which are prepared in a nonradioactive form and may then be subjected to an effective amount of neutron irradiation to produce microspheres containing the desired beta emitting radioisotope; and the provision of methods for carrying out radiation synovectomy of arthritic joints and for preparing biodegradable microspheres for use in radiation synovectomy. Other objects and features will be in part apparent and in part pointed out hereinafter.

Briefly, the present invention is directed to novel radioactive microspheres useful for radiation synovectomy of arthritic joints. These radioactive microspheres comprise a biodegradable or biologically compatible glass material containing a beta radiation emitting radioisotope chemically dissolved therein. In a preferred embodiment, such microspheres have been subjected to an acid wash to produce a sparingly soluble coating on their outer surface so that the microspheres gradually dissolve after they are no longer radioactive.

Another aspect of the invention is the provision of novel microspheres which are initially nonradioactive and which, upon being subjected to an effective amount of neutron irradiation, will produce a beta radiation emitting radioisotope thereby rendering the microspheres suitable for use in radiation synovectomy of arthritic joints while avoiding the handling of radioactive elements during initial production of the microspheres.

A still further aspect of the invention resides in the provisions of novel methods for carrying out radiation synovectomy of arthritic joints utilizing the novel radioactive microspheres of the invention.

DESCRIPTION OF THE PREFERRED EMBODIMENTS

Figure 1:
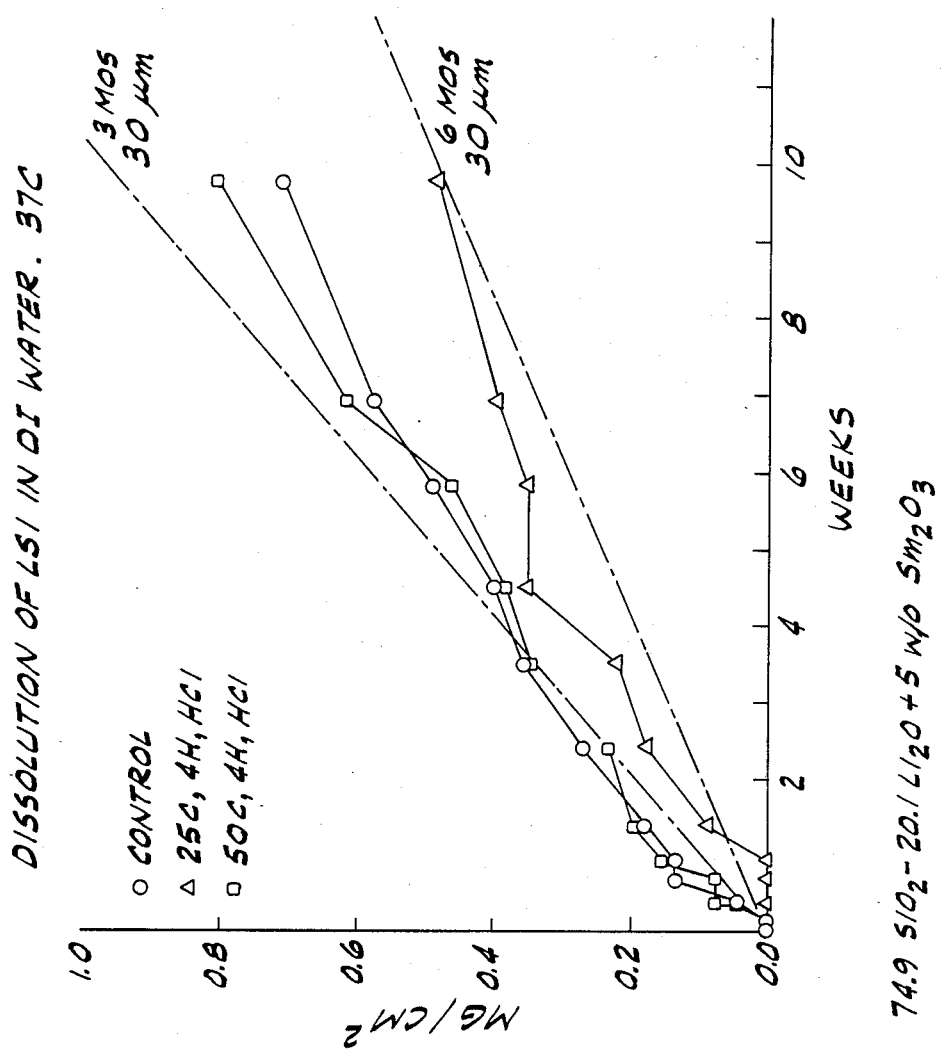
FIGS. 1 and 2 are graphs showing the dissolution (weight loss in mg/cm$^2$) of two different glass compositions of the invention in deionized water at 37° C. as a function of time.

In accordance with the present invention, it has now been found that certain novel radioactive microspheres may be advantageously employed in radiation synovectomy of arthritic joints while substantially avoiding systemic leakage of the beta radiation emitting radioisotope from the joint being treated and permitting greater control of the particle size of such microspheres. The radioactive microspheres of the invention are prepared from novel microspheres which may be manufactured and sized before radioactivity is induced providing the advantage of working only with nonradioactive materials during initial production of the microspheres.

In a first embodiment of the invention, the novel radioactive microspheres are comprised of a biodegradable glass material selected from the group consisting of lithium silicate, lithium aluminosilicate, lithium aluminoborate, lithium germanate and lithium aluminogermanate and containing a beta radiation emitting radioisotope chemically dissolved in and distributed substantially uniformly throughout the glass material, the radioisotope being samarium-153, holmium-166, erbium-169, dysprosium-165, rhenium-186, rhenium-188 or yttrium-90. It has been found that lithium silicate, lithium aluminosilicate, lithium aluminoborate, lithium germanate or lithium aluminogermanate biodegradable glasses are particularly suitable for the purposes of the invention since lithium does not become a gamma emitter upon being subjected to neutron irradiation whereas sodium, calium and phosphorus, components of otherwise biodegradable glasses, do become gamma emitters with unacceptably long half-lives upon neutron irradiation or become beta emitters which have undesirably long half-lives or which bond to bone. For example, the composition of the bioactive and partially biodegradable glass composition known as "Bioglass" is 45% $SiO_2$, 24.5% $Na_2O$, 24.5% $CaO$ and 6% $P_2O_5$ (Hench, Ceramic Implants for Humans, Advanced Ceramic Materials, 1(4):306–324, 1986), and this glass is unsuitable because of the sodium, calcium and phosphorous it contains.

Also, while use of the above-noted lithium glass materials is preferred, potassium glasses selected from the group consisting of potassium silicate, potassium aluminosilicate, potassium aluminoborate, potassium germanate and potassium aluminogermanate may also be used in the practice of the invention. While potassium does become a gamma emitter upon being subjected to neutron irradiation, the radioisotope potassium-42 thus produced has an acceptably short half-life of approxiately 12 hours. Therefore, when such potassium glass materials are employed, administration of the radioactive microspheres containing them is delayed for a sufficient time to permit the potassium-42 to decay to acceptable levels.

The above-noted beta radiation emitting radioisotopes are also particularly suitable for use in the present invention. Samarium-153 (46.3 hr. half-life) and holmium-166 (26.8 hr. half-life) can readily be dissolved in silicate, aluminosilicate or aluminoborate glasses, have good activation properties in a nuclear reactor, possess imageable gamma rays, exhibit low toxicity and have half-lives long enough for distribution of the radioactive microspheres of the invention containing them.

Holmium-166 is produced by neutron capture on 100% abundant, stable holmium-165 with thermal neutron and resonance neutron cross sections of 61.2 and 670 barns, respectively. It decays with a 26.83 hour half-life by emission of 1.855 MeV (51%) and 1.776 MeV (48%) maximum energy beta particles with a maximum range in water of about 8.0 mm and an average range of about 2 mm. Since dysprosium-165 emits a beta particle of slightly lower maximum energy (1.31 MeV) and has proven efficacious in human knee radiation synovectomies, it appears that holmium-166 has sufficient penetration for this application. Ho-166 also emits an 80.5 KeV gamma-ray in 6.2% abundance and thus is imageable by conventional techniques.

Samarium-153 is produced by neutron capture of natural or isotopically enriched samarium-152 with thermal and resonance neutron cross sections of 210 and 3,020 barns, respectively. It decays by beta emissions of 0.810 MeV (20%), 0.710 MeV (49%), and .640 MeV (30%) maximum energies with concomitant ranges of about 2.3 mm maximum and 0.8 mm average distance, respectively. Sm-153 has a physical half-life of 46.27 hours and produces a highly imageable 103 KeV gamma ray with an abundance of 29.8%, decaying to stable Eu-153.

Samarium-153 and holmium-166 are both chemically compatible and capable of being incorporated into many types of glass in which no other significant radioactivities induced by neutron bombardment will be present after about one day of decay. Erbium-169, dysprosium-165, rhenium-186, rhenium-188 (from rhenium-185 and rhenium-187) and yttrium-90 also possess the desired properties rendering them suitable for use as the radioisotope in this embodiment of the invention.

As mentioned, in the first embodiment of the invention generally described above, a biodegradable glass material is selected from the group consisting of lithium silicate, lithium aluminoborate, lithium aluminosilicate, lithium germanate and lithium aluminogermanate or the corresponding potassium glass materials. Such glasses may be doped with samarium oxide ($Sm_2O_3$), holmium oxide ($Ho_2O_3$) or oxide of erbium, dysprosium, rhenium or yttrium in preparing the novel nonradioactive and radioactive microspheres of the invention. By way of example, such biodegradable glasses so doped may have the following illustrative compositions by weight percent:

20.1% $L_2iO$-74.9% $SiO_2$-5% $Sm_2O_3$
21.8% $Li_2O$-3.9% $Al_2O_3$-69.3% $SiO_2$-5% $Sm_2O_3$
19.7% $Li_2O$-13.1% $B_2O_3$-62.2% $SiO_2$-5% $Sm_2O_3$

It will be understood that other lithium silicate, lithium aluminosilicate, lithium aluminoborate, lithium germanate and lithium aluminogermanate glass materials or the corresponding potassium glass materials suitably doped with samarium, holmium, erbium, dysprosium, rhenium or yttrium may also be used in the practice of the invention.

In a second embodiment of the invention, the novel radioactive microspheres are comprised of a biologically compatible glass material selected from the group consisting of magnesium aluminosilicate and aluminosilicate glass material and containing a beta radiation emitting radioisotope chemically dissolved in and distributed substantially uniformly through the glass material, the radioisotope being samarium-153, holmium-166, erbium-169, dysprosium-165, rhenium-186 or rhenium-188. While such glass materials are not biodegradable, they are biologically compatible and are useful in the practice of the invention. Such glass compositions may be prepared by doping magnesium aluminosilicate or aluminosilicate glass materials with oxides of samarium ($Sm_2O_3$), holmium ($Ho_2O_3$), erbium ($Er_2O_3$), dysprosium ($Dy_2O_3$), or rhenium ($ReO_2$). Illustrative specific examples of such glass compositions include the following compositions by weight percent.

20% MgO-21% Al$_2$O$_3$-52% SiO$_2$-7% Sm$_2$O$_3$
40% Y$_2$O$_3$-20% Al$_2$O$_3$-40% SiO$_2$
40% Sm$_2$O$_3$-20% Al$_2$O$_3$-40% SiO$_2$
20% MgO-21% Al$_2$O$_3$-52% SiO$_2$-7% Ho$_2$O$_3$
20% MgO-21% Al$_2$O$_3$-52% SiO$_2$-7% ReO$_2$

It will be understood that other magnesium aluminosilicate or aluminosilicate glass materials suitably doped with samarium, holmium, erbium, dysprosium or rhenium may also be used in the practice of the invention.

The microspheres of the present invention may be prepared from a homogeneous mixture of powders (i.e. the batch) that is melted to form the desired glass composition. The exact chemical compounds or raw materials used for the batch is not critical so long as they provide the necessary oxides in the correct proportion for the melt composition being prepared. For example, if a samarium doped lithium silicate glass is being made, then Sm$_2$O$_3$, Li$_2$CO$_3$ and SiO$_2$ powders would be used as the batch raw materials. The purity of each raw material is typically greater than 99.9%. After either dry or wet mixing of the powders to achieve a homogeneous mixture, the mixture may be placed in a platinum crucible for melting. High purity alumina crucibles can also be used if at least small amounts of alumina can be tolerated in the glass being made. The raw materials must not contain impurities that become radioactive from neutron irradiation.

The crucibles containing the powdered batch are then placed in an electric furnace heated to 1500° to 1600° C. depending upon the composition. In this temperature range, the batch melts to form a liquid which is stirred several times to improve its chemical homogeneity. The melt should remain at 1500° to 1600° C. until all the solid batch is totally dissolved. This usually requires 2 to 5 hours duration. When melting and stirring is complete, the crucible is removed from the furnace and the melt is quickly quenched to a glass by pouring the melt onto a cold steel plate or into cold clean water. This procedure breaks the glass into fragments, which aids and simplifies crushing the glass to a fine powder (less than 400 mesh). The powder is then sized and spheridized for use.

The quenched and broken glass is first crushed to about minus 100 mesh particle size using a mortar and pestle. The minus 100 mesh material is then ground using a mechanized mortar and pestle or ball mill until it passes a 400 mesh sieve. The minus 400 mesh particles (37 microns in diameter) may be stored in a dry container until used.

The particles are formed into glass microbeads or microspheres by introducing the minus 400 mesh particles into a gas/oxygen flame where they are melted and a spherical liquid droplet is formed by surface tension. This droplet is rapidly cooled before it touches any solid object so that its spherical shape is retained in the solid. Just prior to spheridizing, the minus 400 mesh powder is rescreened through a 400 mesh sieve to destroy any large agglomerates that may have formed during storage. The minus 400 mesh powder is then placed in a vibratory feeder located above the gas/oxygen burner. The powder is slowly vibrated into a vertical glass tube which guides the powder particles directly into the hot flame of the gas/oxygen burner. A typical rate for feeding the powder to the flame is 5 to 25 grams/hour with the described apparatus. The flame of the burner is directed into a small metal container which catches the small glass beads or spheres as they are expelled from the flame.

After spheridization, the glass spheres are collected and rescreened with a sonic sifter. For use in the present invention, the fraction in the range of 3 to 30 microns in diameter is recovered since this is the desirable size for use in radiation synovectomy of arthritic joints. After screening, the microspheres in this size range are examined with an optical microscope and are then washed with a weak acid (HCl, for example), filtered and washed several times with reagent grade acetone. The washed beads or spheres are then heated in a furnace in air to 500°-600° C. for 2-6 hours to destroy any organic material therein.

The final step is to examine a representative sample of the microspheres in the selected size range or fraction in a scanning electron microscope. The size, range and shape of the beads or spheres are evaluated, and the quantity of undersize beads (less than 3 microns in diameter) is determined along with the concentration of non-spherical particles. The composition of the beads can be checked by energy dispersive x-ray analysis to confirm that the composition is correct and that there is an absence of chemical contamination.

The glass microspheres are then ready for activation by being subjected to an effective amount of neutron irradiation which will produce a beta radiation emitting radioisotope of samarium-153, holmium-166, erbium-169, dysprosium-165, rhenium-186, rhenium-188 or yttrium-90, the amount depending upon the particular isotope of these elements that has been chemically dissolved and uniformly distributed throughout the glass material. The resulting radioactive microspheres of the invention have beta radiation emitting energies highly suitable for radiation synovectomy of arthritic joints and also provide gamma ray emissions suitable for nuclear medicine imaging devices.

In accordance with the invention, the radioactive microspheres prepared as described may be administered to the afflicted joints by intra-articular injection or by other suitable means of administration. The microspheres are believed to be chemically durable in joint fluids and mechanically contained within the joint cavity. Moreover, upon administration, they become distributed reasonably uniformly along the synovial membrane and emit beta radiation of sufficient range to fully or substantially fully irradiate the thickness of the membrane without giving significant dosage to more distant joint structures. Also, inasmuch as the thickness of the diseased membrane varies in different joints, the present invention makes possible the preparation of microspheres doped with a different energy beta emitter for a finger joint than for a knee, for example.

Further, the present invention provides smooth microspheres which constitute a preferred shape over irregular, jagged particles with sharp edges and corners for the purpose of radiation synovectomy of arthritic joints. The smooth surface of a sphere should be more tissue compatible and less irritating than other shapes. The smooth shape of the microspheres of the invention should also cause less friction, mechanical wear and inflammation in a joint with moving parts than irregularly shaped particles. Heretofore, radioactive microspheres of the type provided by the present invention have not been available nor have glass microspheres of this type been injected into arthritic joints of humans or animals.

While, as indicated, the microspheres of the present invention may be of various sizes, it is preferred for radiation synovectomy of arthritic joints that the microspheres have a diameter within the range of about 3 to 30 micrometers (microns).

To localize the desired radiation to the affected joint, the radioactive element is chemically dissolved in a host glass material which is insoluble in the body. The escape or leakage of the radioactive material from the joint has been a major problem with other types of materials (e.g. colloids) previously used in this type of radiation therapy and an insoluble glass should prevent any leakage since the radioactive material cannot escape from insoluble glass microspheres. Also, for use in human joints, there is a perceived advantage to using glass beads or microspheres which gradually dissolve after they are no longer radioactive, i.e. which are biodegradable. Accordingly, in accordance with the present invention, it is preferred to employ the biodegradable glass microspheres which are initially insoluble during the period of time the bead is radioactive (i.e. few weeks) and which then gradually starts to dissolve and eventually disappear.

Biodegradable glass microspheres having such desired characteristics may be prepared through another aspect of the present invention by treating the above-described biodegradable lithium silicate, lithium aluminosilicate, lithium aluminoborate, lithium germanate, lithium aluminogermanate or corresponding potassium glass microspheres in such a way as to form an insoluble or sparingly soluble coating on its outer surface. This can be done by washing such glasses in common acids such as hydrochloric acid, nitric acid or sulfuric acid and thereby replace the lithium or potassium ions on the outer surface with protons or $H_3O^+$. The results of this dealkalization process is to produce a thin layer (skin) on the surface of the glass beads or microspheres whose solubility is less than than of the underlying glass. A glass bead with such a dealkalized surface initially dissolves slowly until the more durable outer surface layer is dissolved, and then starts to dissolve faster as the less durable, underlying glass is exposed to the surrounding media.

Thus, washing glass microspheres of the invention in common acids is an exemplary and practical means of achieving the desired dissolution characteristics required for radioactive, biodegradable glass microspheres for use in human joints. It will be understood by those skilled in the art that various factors are important to the dissolution characteristics of the dealkalized surface or skin. These are: (1) the starting glass composition, especially the amount of alkali ion (i.e. lithium or potassium) present; (2) concentration and type of acid employed; (3) temperature of the acid; (4) time of acid treatment; and (5) heat treatment of dealkalized surface after acid wash. It will also be understood by those skilled in the art that in addition to acid washing, other procedures such as heating a glass in various gases such as $SO_2$ and $F_2$ can be used to produce a more chemically durable dealkalized skin on the lithium and potassium glasses described above.

The following examples further illustrate the invention.

EXAMPLE 1

31 rabbits were injected with about 5 mg each of non-radioactive glass microspheres (20–30 microns in size) having the composition by weight: 40% $Y_2O_3$–20% $Al_2O_3$–40% $SiO_2$. The injections were made in the left stifles (knee) using Angiovist 370 contrast medium (diatrizoate meglumine and diatrizoate sodium; Berlex Laboratories, Incorporated) as a suspending medium, with a control injection of Angiovist in the right stifle. The rabbits showed no ill effects whatsoever over periods ranging from 48 hours to three months. Upon sacrifice at intervals of 2 to 90 days, the stifles were all dissected and slides prepared of various joint tissues. Examination of the slides revealed microspheres only along the synovium with no spheres apparent in the underlying fat tissue or lymph nodes, and no mechanical abrasion or damage to the cartilage or other joint structures.

EXAMPLE 2

Figure 2:
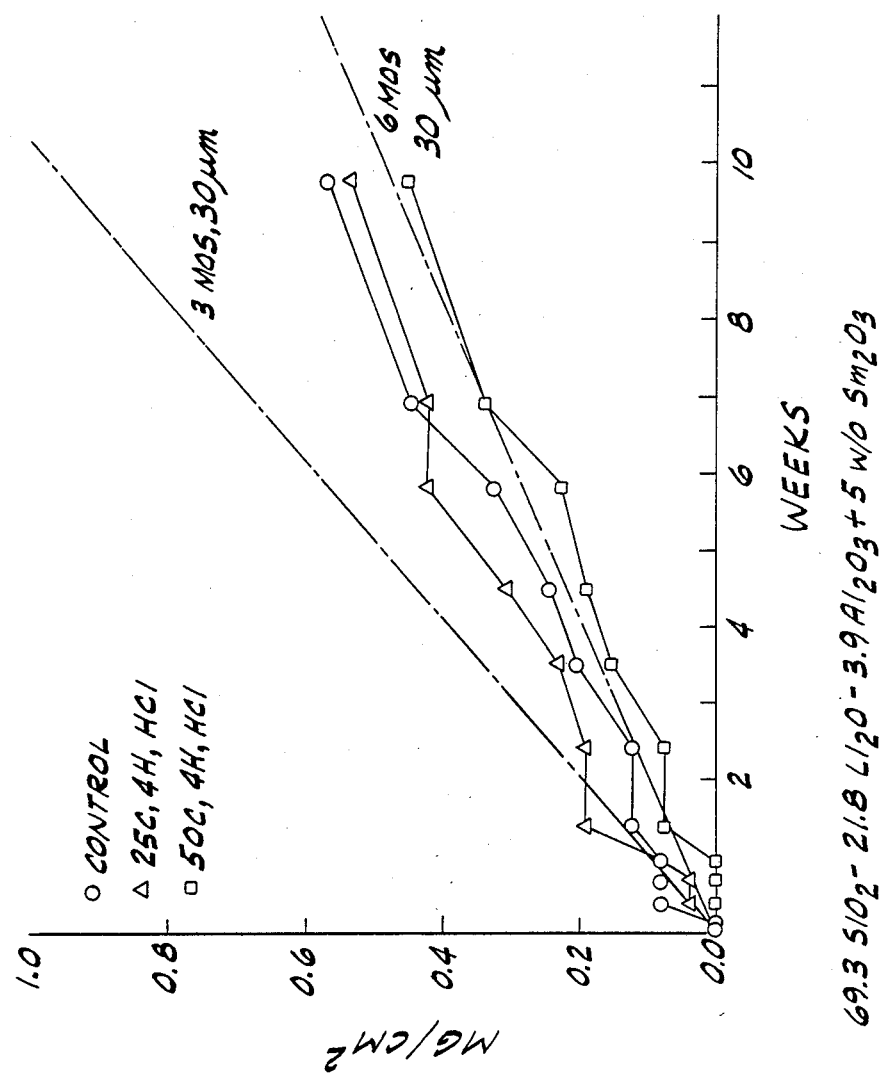

FIGS. 1 and 2 show the dissolution (weight loss in $mg/cm^2$) of two different glass compositions as shown thereon in deionized water at 37° C. as a function of time. The straight lines labeled 3 mos. and 6 mos. designate the dissolution needed for a 30 micron bead or sphere to dissolve in 3 and 6 months, respectively. In addition to untreated specimens (control), each figure also shows the dissolution of specimens of each glass composition washed in 1 N HCl for 4 hours at either 25° or 50° C.

The effectiveness of the acid wash in reducing the dissolution at short times is clearly evident in FIG. 1 for the specimen washed in HCl at 25° C. In contrast to the unwashed control which showed an immediate weight loss, the sample washed in acid at 25° C. did not show any detectable weight loss for more than one week in deionized water. After about one week, the sample then began to dissolve as desired. Similar results are given in FIG. 2, except that acid washing at 50° C. was more effective for this glass because of its different composition.

These studies show that acid washing produces an insoluble surface skin which yields the dissolution characteristics needed for radioactive, biodegradable glass microspheres for use in human joints.

EXAMPLE 3

A. SAMPLE PREPARATION

The glass compositions in the following table were prepared from reagent grade chemicals. Batches yielding 50 grams of glass were melted in platinum crucibles in an electric furnace at approximately 1350° C. The melt was held at 1350° C. for 1 to 2 h for fining and homogenization and then cast into steel molds to form bars measuring approximately $1 \times 1 \times 8$ cm which were annealed at 500° C. for 30 min. and then slowly cooled to room temperature. Slabs approximately $0.2 \times 1 \times 1$ cm were cut from the bars and ground to rectangular shape using 180 grit silicon carbide paper.

| | COMPOSITION OF GLASSES | | | |
|---|---|---|---|---|
| | Batch Composition (Weight %) | | | |
| Glass | $SiO_2$ | $Li_2O$ | $Al_2O_3$ | $SM_2O_3$ |
| LS1 | 74.9 | 20.1 | 0.0 | 5.0 |
| LS3 | 69.3 | 21.8 | 3.9 | 5.0 |

A portion of the LS1 glass was broken and ground to $-200$ mesh and wet milled for 6 h with methanol. The powder was then dried and screened through a 325 mesh sieve. The $-325$ mesh glass powder was slowly fed into an oxygen/propane flame where surface tension caused the molten particles to become spheres.

B. SURFACE TREATMENTS

1. Sulfur Dioxide Gas

The glass slabs were placed in a tube furnace at either 400° or 500° C. $SO_2$ gas was bubbled through water at 25° C. at an approximate rat of one bubble per second before flowing through the furnace. The treatment times were 90 min. at 400° C. and 15 or 45 min. at 500° C. After removal from the furnace, the slabs were cooled, rinsed in distilled water to remove any lithium sulphate formed on the surface, and dried in an oven at 100° C.

2. Washing in HCl

The glass was placed in a 0.1N HCl solution in a beaker, magnetically stirred, rinsed in distilled water, and dried in air at 100° C. Initially, the effect of acid washing on the glasses for 2, 4, 6 or 8 h at 25° C., 50° C., or 75° C. was examined. The time and temperature which gave the longest delay before dissolution commenced for LS1 was 4 h at 25° C. an for LS3 was 4 h at 50° C. These times and temperatures were used in subsequent heat treatments.

3. Washing in HCl Followed by Heat Treatment

After washing in 0.1 N HCl acid, the glass slabs were heated on a steel plate in a furnace to 350° or 400° C. At 350° C., the slabs were heated for 10 or 30 min. and at 400° C., the slabs were heated for 10, 30, 45, 60, or 90 min. Microspheres of LS1 were heated at 350° C. for 30 min.

C. CHEMICAL DISSOLUTION MEASUREMENTS

After surface treatments, the glass slabs were weighed and their exact dimensions measured before placing them in polyethylene bottles containing 125 mL of distilled water (pH=7). The bottles were placed in an oven at 37° C., which is the temperature of the human body. The weight change of each slab was measured periodically by removing the slab from the bottle, drying it in an oven at 100° C., and weighing.

The average dissolution, D, of each sample was calculated from the equation $$D = (W_o - W)/A$$

where $W_o$ was the initial weight of the original slab, W was the current weight of the slab, and A was the surface area of the slab. The dissolution was plotted against time.

Approximately 20 mg of microspheres made from the LS1 glass were placed in polyethylene bottles containing 25 mL of distilled water and placed in an oven at 37° C. The microspheres were removed after 3 weeks for SEM analysis.

D. SEM ANALYSIS

Selected microspheres and slabs were mounted on a steel cylinder for SEM analysis. The slabs were broken and one piece was mounted to observe the corroded surface and the other to observe the fresh fracture surface. The mounted slabs and microspheres were vapor coated with palladium.

Because the as-cut slabs had a very rough surface, polished slabs were used to see the effects of surface treatments. The surface of slabs of each glass was polished to 1 micron using silicon carbide polishing paper and finally one micron $Al_2O_3$. These slabs were left untreated, treated in acid, or treated in acid followed by heat treatment (LS1: 350° C. for 30 minutes, LS3: 400° C. for 45 minutes). These samples were examined by SEM to determine if there was any change in the surface due to washing in acid or washing in acid followed by heat treatment.

E. RESULTS AND CONCLUSIONS

LS1 glass which contains 74.9% $SiO_2$, 20.1% $Li_2O$, and 5.0% $Sm_2O_3$ (weight %) is well suited for microspheres that could be irradiated to treat rheumatoid arthritis. Acid washing followed by heating LS1 reduced the dissolution to zero. Glasses acid washed and heated at 400° C. remained insoluble after 6 months. LS1 glass acid washed then heated for 10 min. at 350° C. remained insoluble for 4 weeks and then began to dissolve at approximately half of the rate calculated for a 30 micron sphere to dissolve in 6 months. If this glass continued to dissolve at this rate, then a 30 micron sphere treated in this way should be totally dissolved in 12 months. Acid washing followed by heat tretment of LS1 glass for 10 min. for 350° C. appears to create a temporarily insoluble surface layer which should prevent the release of radioactive Sm-153.

SEM photographs of polished LS3 glass shows that acid washing followed by heating causes the surface to crack. This is probably due to a difference in thermal expansion between the bulk glass and the dealkalyzed layer. Acid washed then heated LS3 glasses began to dissolve immediately confirming no protective layer was created. In LS3 glass acid washed then heated at 400° C., the initial dissolution rate paralleled the acid washed glass. After a few weeks, the dissolution decreased to almost zero, suggesting the corrosion process caused a protective layer to develop.

Washing LS1 and LS3 glass in 0.1N HCl delays the dissolution of LS3 for 5 days and of LS1 for 7 days. Dissolution then begins at approximately the same rate as the untreated glass.

Exposure to hot sulfur dioxide gas decreases the dissolution of LS1 glass in water at 37° C. but does not significantly affect the dissolution of LS3. No delay in dissolution occurred for either glass. Decreasing the temperature of the $SO_2$ treatment may facilitate the dealkalyzing reactions of the $SO_2$ and improve the chemical durability of the surface.

SEM photographs confirm that the acid washed then heated slabs of LS1 which had a zero dissolution rate show no effect of corrosion, while the acid washed and untreated slabs showed cracking after two weeks in water.

EXAMPLE 4

About 10 mg. of non-biodegradable glass microspheres (10–20 microns in size) having the composition by weight: 20% MgO-21% $Al_2O_3$-52% $SiO_2$-7% $Sm_2O_3$, were irradiated 10 minutes in a neutron flux of 4E13/square cm/sec to make about 300 microcuries of Sm-153. The microspheres were irradiated in sealed, high density polyethylene vials having a volume of slightly more than 1 cc and drawn into 1 cc tuberculin syringes using Angiovist contrast medium as a suspending agent and injected into the stifles of healthy rabbits. Serial imaging was performed to ascertain leakage.

Significant leakage was observed down the leg of the first four rabbits, but this appeared to occur due to leakage out of the injection puncture and possible tear in the joint capsule. A fifth rabbit injected through the cartilage in the front of the knee (i.e. through a thicker, self-sealing portion of the joint) exhibited no leakage.

In view of the above, it will be seen that the several objects of the invention are achieved and other advantageous results attained.

As various changes could be made in the above products and methods without departing from the scope of the invention, it is intended that all matter contained in the above description or shown in the accompanying drawings shall be interpreted as illustrative and not in a limiting sense.

What is claimed is:

1. A method for carrying out radiation synovectomy of arthritic joints which comprises administering to a mammal affected with an arthritic joint an effective amount of microspheres comprising a biologically compatible material selected from the group consisting of aluminosilicate, magnesium aluminosilicate, lithium silicate, lithium aluminosilicate, lithium aluminoborate, lithium germanate, lithium aluminogermanate, potassium silicate, potassium aluminosilicate, potassium aluminoborate, potassium germanate and potassium aluminogermanate and containing a beta radiation emitting radioisotope chemically dissolved in and distributed substantially uniformly throughout said glass material and being selected from the group consisting of samarium-153, holmium-166, erbium-169, dysprosium-165, rhenium-186, rhenium-188 and yttrium-90.

2. A method as set forth in claim 1 wherein said glass material is lithium silicate and said radioisotope is samarium-153.

3. A method as set forth in claim 1 wherein said glass material is lithium aluminosilicate and said radioisotope is samarium-153.

4. A method as set forth in claim 1 wherein said glass material is lithium aluminoborate and said radioisotope is samarium-153.

5. A method as set forth in claim 1 wherein said glass aterial is lithium silicate and said radioisotope is holmium-166.

6. A method as set forth in claim 1 wherein said glass material is lithium aluminosilicate and said radioisotope is holmium-166.

7. A method as set forth in claim 1 wherein said glass material is lithium aluminoborate and said radioisotope is holmium-166.

8. A method as set forth in claim 1 wherein said glass material is magnesium aluminosilicate and said radioisotope is samarium-153.

9. A method as set forth in claim 1 wherein said glass material is aluminosilicate and said radioisotope is samarium-153.

10. A method as set forth in claim 1 wherein said glass material is aluminosilicate and said radioisotope is yttrium-90.

11. A method as set forth in claim 1 wherein said microsphere has a diameter in the range of about 3 to about 30 micrometers.

12. A radioactive microsphere for radiation synovectomy of arthritic joints in a mammal comprising a biologically compatible glass material selected from the group consisting of magnesium aluminosilicate and aluminosilicate and containing a beta radiation emitting radioisotope chemically dissolved in and distributed substantially uniformly throughout said glass material and being selected from the group consisting of samarium-153, holmium-166, erbium-169, dysprosium-165, rhenium-186 and rhenium-188.

13. A radioactive microsphere as set forth in claim 12 wherein said glass material is magnesium aluminosilicate and said radioisotope is samarium-153.

14. A radioactive microsphere as set forth in claim 12 wherein said glass material is aluminosilicate and said radioisotope is samarium-153.

15. A radioactive microsphere as set forth in claim 12 wherein said glass material is magnesium aluminosilicate and said radioisotope is holmium-166.

16. A radioactive microsphere as set forth in claim 12 wherein said glass material is aluminosilicate and said radioisotope is holmium-166.

17. A radioactive microsphere as set forth in claim 12 wherein said microsphere has a diameter in the range of about 3 to about 30 micrometers.

18. A radioactive microsphere for radiation synovectomy of arthritic joints in a mammal comprising a biodegradable glass material selected from the group consisting of lithium silicate, lithium alumino-silicate, lithium aluminoborate, lithium germanate and lithium aluminogermanate and containing a beta radiation emitting radioisotope chemically dissolved in and distributed substantially uniformly throughout said glass material and being selected from the group consisting of samarium-153, holmium-166, erbium-169, dysprosium-165, rhenium-186, rhenium-188 and yttrium-90.

19. A radioactive microsphere as set forth in claim 18 wherein said glass material is lithium silicate and said radioisotope is samarium-153.

20. A radioactive microsphere as set forth in claim 18 wherein said glass material is lithium aluminosilicate and said radioisotope is samarium-153.

21. A radioactive microsphere as set forth in claim 18 wherein said glass material is lithium aluminoborate and said radioisotope is samarium-153.

22. A radioactive microsphere as set forth in claim 18 wherein said glass material is lithium silicate and said radioisotope is holmium-166.

23. A radioactive microsphere as set forth in claim 18 wherein said glass material is lithium aluminosilicate and said radioisotope is holmium-166.

24. A radioactive microsphere as set forth in claim 18 wherein said glass material is lithium aluminoborate and said radioisotope is holmium-166.

25. A radioactive microsphere as set forth in claim 18 wherein said microsphere has a diameter in the range of about 3 to about 30 micrometers.

* * * * *